(12) United States Patent
Izraelev

(10) Patent No.: US 6,206,659 B1
(45) Date of Patent: Mar. 27, 2001

(54) MAGNETICALLY DRIVEN ROTOR FOR BLOOD PUMP

(75) Inventor: Valentin M. Izraelev, Eden Prairie, MN (US)

(73) Assignee: Advanced Bionics, Inc., Hopkins, MN (US)

(*) Notice: Subject to any disclaimer, the term of this patent is extended or adjusted under 35 U.S.C. 154(b) by 0 days.

(21) Appl. No.: 08/886,185

(22) Filed: Jul. 1, 1997

Related U.S. Application Data

(63) Continuation of application No. 08/456,503, filed on Jun. 1, 1995, now Pat. No. 5,685,700.

(51) Int. Cl.[7] .................................................. F04B 17/00
(52) U.S. Cl. .................... 417/420; 417/356; 417/423.14; 415/900; 416/186.12
(58) Field of Search .................................. 415/203, 206, 415/900; 600/16; 604/4, 131, 151; 417/420, 423.14, 356, 357, 423.7, 424.1; 623/3; 416/186.12, 189

(56) References Cited

U.S. PATENT DOCUMENTS

| | | |
|---|---|---|
| 2,319,730 | 5/1943 | Garraway . |
| 3,433,163 | 3/1969 | Sheets et al. . |
| 3,647,324 * | 3/1972 | Rafferty et al. ................... 417/420 |
| 3,890,019 | 6/1975 | Boden et al. . |
| 3,957,389 | 5/1976 | Rafferty et al. . |
| 3,970,408 | 7/1976 | Rafferty et al. . |
| 4,036,565 | 7/1977 | Becker . |
| 4,057,369 | 11/1977 | Isenberg et al. . |
| 4,507,048 * | 3/1985 | Belenger et al. ................... 415/90 |
| 4,688,998 | 8/1987 | Olsen et al. . |
| 4,779,614 | 10/1988 | Moise . |
| 4,944,748 | 7/1990 | Bramm et al. . |
| 4,994,078 | 2/1991 | Jarvik . |
| 4,995,857 | 2/1991 | Arnold . |
| 5,049,134 | 9/1991 | Golding et al. . |
| 5,055,005 | 10/1991 | Kletschka . |

(List continued on next page.)

FOREIGN PATENT DOCUMENTS

| | | |
|---|---|---|
| 2342767 | 3/1975 | (DE) . |
| 3130974 A1 | 2/1983 | (DE) . |
| 1359007 | 7/1974 | (GB) . |

OTHER PUBLICATIONS

Olsen et al., "Blood Pump with a Magnetically Suspended Impeller", *Trans. Am. Soc. Artif. Intern. Organs*, vol. XXXI, 1985, pp. 395–401.

(List continued on next page.)

*Primary Examiner*—Charles G. Freay
(74) *Attorney, Agent, or Firm*—Haugen Law Firm PLLP

(57) ABSTRACT

A pump for transferring fragile and aggressive fluids such as human blood and comprising a pumping chamber along with a pair of fluid inlet ports arranged in oppositely disposed relationship on the chamber, and at least one outlet port arranged transversely and medially of the inlet ports. A rotor assembly is positioned within the pumping chamber having a core in the form of a first surface of revolution and having a dual-conical configuration converging toward opposed polar end regions and with an axis of rotation extending between the polar regions. At least one shroud is provided spaced outwardly of the surface of the core, with medial vanes being positioned between the surface of the core and shroud, the shroud defining a second surface of revolution coaxially with the axis of the core. The rotor assembly includes magnets which are arranged at radially spaced locations and with a magnetic drive positioned to deliver rotational driving energy to the rotor. The sole support for the rotor assembly are the hydrodynamic forces acting upon the assembly during its operation, with the rotor assembly body having a relative density of between 10% and 90% of the relative density of the fluid being pumped.

9 Claims, 4 Drawing Sheets

U.S. PATENT DOCUMENTS

| | | |
|---|---|---|
| 5,078,741 | 1/1992 | Bramm et al. . |
| 5,112,200 | 5/1992 | Isaacson et al. . |
| 5,158,440 | 10/1992 | Cooper et al. . |
| 5,195,877 | 3/1993 | Kletschka . |
| 5,205,721 | 4/1993 | Isaacson . |
| 5,211,546 | 5/1993 | Isaacson et al. . |
| 5,326,344 | 7/1994 | Bramm et al. . |
| 5,385,581 | 1/1995 | Bramm et al. . |
| 5,443,503 | 8/1995 | Yamane . |
| 5,470,208 | 11/1995 | Kletschka . |

OTHER PUBLICATIONS

Bramm et al., "The Sealless and Bearingless Rotor Blood Pump System: Adaptation . . . Thermal Heat Up" Assisted Circulation 3, F. Unger (Ed.), Springer–Verlag Berlin Heidelberg, 1989, pp. 215–224.

Ohara et al., "The Next Generation Baylor C–Gyro Pump: Anthithrombogenic 'Free Impeller' Design for Long–Term Centrifugal VAD", Artif. Organs, vol. 18, #3, 1994, pp. 238–243.

Treichler et al., "A Fluid Dynamic Analysis of a Rotary Blood Pump for Design Improvement", Artif. Organs, vol. 17, No. 9, 1993, pp. 797–808.

Nishida et al., "Development of the Terumo Capiox Centrifugal Pump and Its Clinical . . . Roller Pump", Artif. Organs, vol. 17, No. 4, 1993, pp. 323–327.

Araki et al., "A Flow Visualization Study of Centrifugal Blood Pumps Developed for Long–Term Usage", Artif. Organs, vol. 17, No. 5, 1993, pp. 307–312.

Bramm et al., "Reduction of Coagulation and Hemolysis . . . for Long–Term Application", pp. 175–179.

Sasaki et al., "A Compact Centrifugal Pump for Cardiopulmonary Bypass", Artif. Organs, vol. 16, No. 6, 1992, pp. 592–598.

Ohara et al., "An Ultimate Compact, Seal–less Centrifugal Ventricular Assist Device: Baylor C–Gyro Pump", Artif. Organs, vol. 18, No. 1, 1994, pp. 17–24.

Makinouchi et al, "Internal Hydraulic Loss in a Seal–less Centrifugal Gyro Pump", Artif. Organs, vol. 18, No. 1, 1994, pp. 25–31.

Kijima, et al, "The Margin of Safety in the Use of a Straight Path Centrifugal Blood Pump", Artif. Organs, vol. 18, No. 9, 1994, pp. 680–686.

Araki et al, "A Flow Visualization Study of the NCVC Centrifugal Blood Pump", Artif. Organs, vol. 18, No. 9, 1994, pp. 669–672.

Kabei et al, "Concept Designs of Nonrotating–type Centrifugal Blood Pump . . . Disc–type Centrifugal Pump", Artif. Organs, vol. 18, No. 9, 1994, pp. 657–663.

Schima et al., "The Vienna Implantable Centrifugal Blood Pump", Artif. Organs, vol. 18, #7, 1994, pp. 500–505.

Akamatsu et al., "Centrifugal Blood Pump with a Magnetically Suspended Impeller", Artif. Organs, vol. 16, No. 3, 1993, pp. 305–308.

Miller et al., "Evaluation of Multiple Disk Centrifugal Pump as an Artificial Ventricle", Artif. Organs, vol. 17, No. 7, 1993, pp. 590–592.

Ohara et al., "Baylor Gyro Pump: A Completely Seal–less . . . Long–Term Circulatory Support", Artif. Organs, vol. 17, No. 7, 1993, pp. 599–604.

Schima et al., "In Vitro Investigation of Thromboenesis in Rotary Blood Pumps", Artif. Organs, vol. 17, No. 7, 1993, pp. 605–608.

Kijima et al., "A Straight Path Centrifugal Blood Pump Concept in the Capiox Centrifugal Pump", Artif. Organs, vol. 17, No. 7, 1993, pp. 593–598.

Naito et al., "Developments of the Baylor–Nikkiso Centrifugal Pump with . . . Circulatory Support", Artif. Organs, vol. 17, No. 7, 1993, pp. 614–618.

Damm et al., "In Vitro Performance of the Baylor/NASA Axial Flow Pump", Artif. Organs, vol. 17, #7, 1993, pp. 609–613.

Yada et al., "Clinical Experience Using the Bio–Pump for Extracorporeal Circulation during Open–Heart Surgery", Artif. Organs, vol. 17, No. 7, 1993, pp. 619–624.

Nishida et al., "Clinical Experience of Assisted Circulation with . . . Women's Medical College", Artif. Organs vol. 17, No. 7, 1993, pp. 625–629.

Curtis et al., "Clinical Experience with the Sarns Centrifugal Pump", Artif. Organs, vol. 17, No. 7, 1993 pp. 630–633.

Affeld et al., "A New Electrohydraulic Energy Concerter for a Left Ventricular Assist Device", Artif. Organs, vol. 18, No. 7, 1994, pp. 479–483.

Curtis et al., "Frequency of Seal Disruption with the Sarns Centrifugal Pump in Postcardiotomy Circulatory Assist", Artif. Organs, vol. 18, No. 3, 1994, pp. 235–237.

* cited by examiner

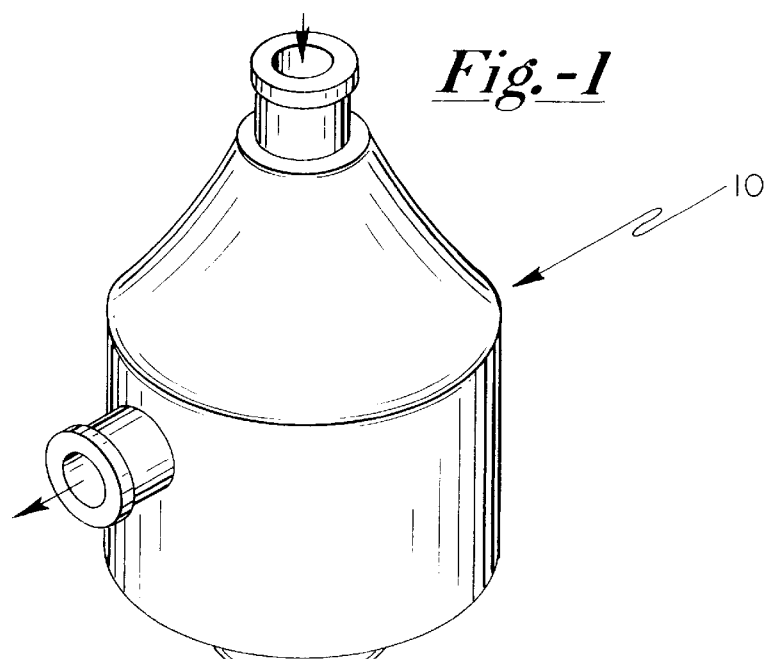
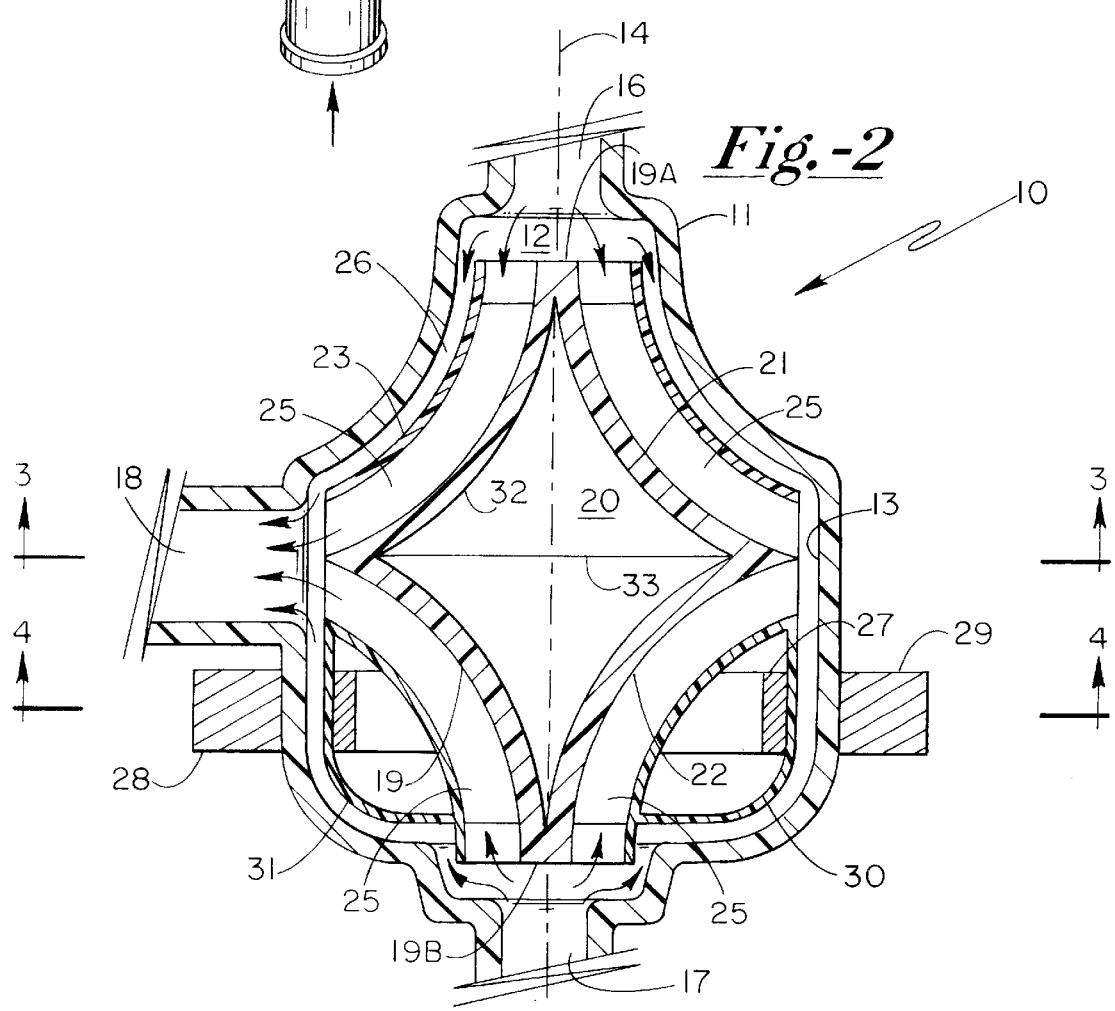

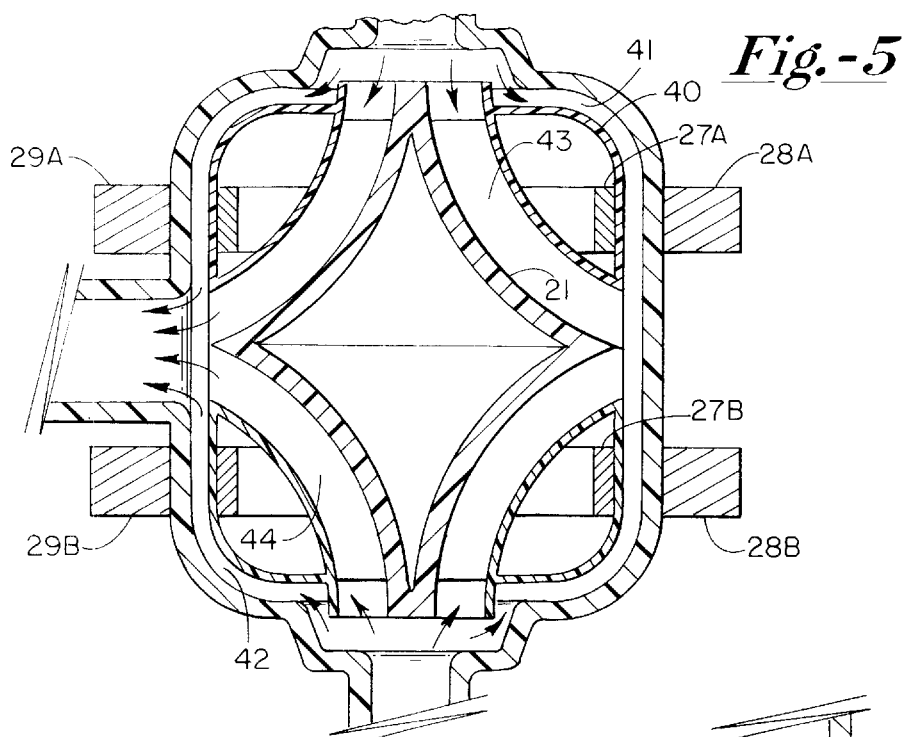
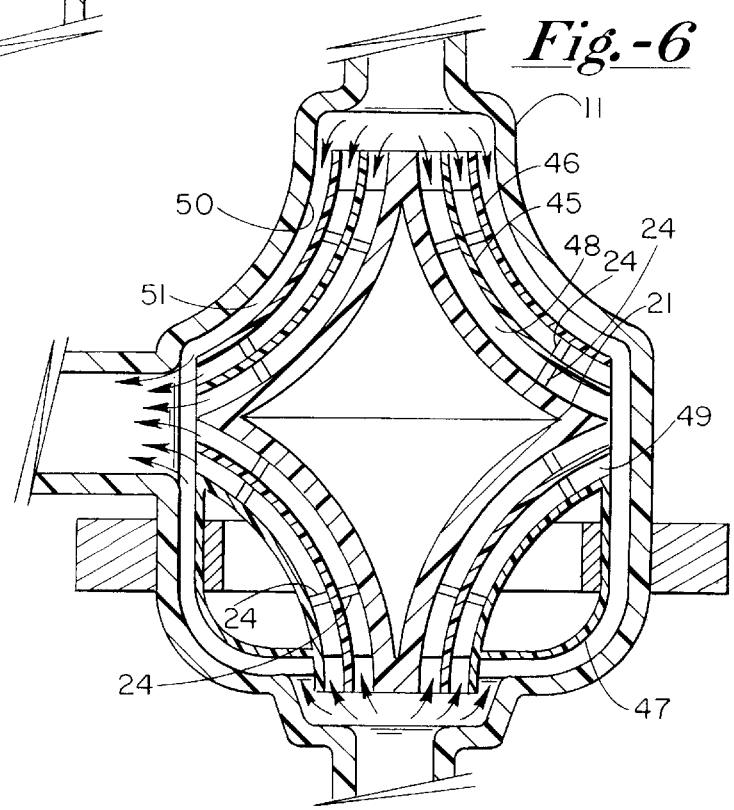

MAGNETICALLY DRIVEN ROTOR FOR BLOOD PUMP

CROSS-REFERENCE TO RELATED APPLICATION

The present application is a continuation-in-part of my application Ser. No. 08/456,503, filed Jun. 1, 1995, entitled "BLOOD PUMP" now U.S. Pat. No. 5,685,700, issued Nov. 11, 1997 and assigned to the same assignee as the present invention.

BACKGROUND OF THE INVENTION

The present invention relates generally to an improved rotor structure for implementation as a pump for transferring fragile or aggressive fluids. Examples of fragile fluids include human or animal blood, neither of which can tolerate exposure to unusual impact and/or sheer forces. Aggressive fluids include corrosive or poisonous fluids, as well as fluids which cannot tolerate contamination, or which otherwise may destroy seals and/or bearings to reduce the lifetime and/or longevity of the pump structure. Poisonous fluids, for example, are extremely dangerous if a leak develops. More particularly, the present invention relates to a rotor for a pump which is bearing and seal-free and wherein the rotor has a core body with one or more shrouds coupled to the outer surface of the core and arranged in parallelly disposed relationship with the outer surface of the core. In addition, the rotor is dynamically balanced by a combination of hydrodynamic and buoyant forces. In this configuration, the design of the rotor provides a plurality of parallelly arranged flow channels through which a fluid contacting area is provided for enhancing flow. In the other configuration, the vanes are presented between the core and the shroud, or between the shrouds for enhancing flow. In the configuration utilizing multiple shrouds, a primary flow channel will be created between the shroud and the core, with a secondary flow channel being arranged outside of the shroud. The primary channel provides meridional channels, while the secondary flow channel provides communication for flow between the inlet and the outlet.

The pump of the present invention is particularly adapted for transferring human blood and is capable of creating a flow of such liquids without damaging and/or otherwise adversely affecting the quality of the material being pumped. The rotor employed in the pump of the present invention including its multiple flow channels is rotated electromagnetically by means of an electromagnetic drive system operating in conjunction with one or more arrays of permanent magnets disposed on the rotor in a brushless motor configuration. Alternatively, a permanent magnet-to-permanent magnet coupling may be employed. As such, the arrangement of the present invention is capable of achieving relative rotation while at the same time being bearing and seal-free.

In the past, pumps and pumping systems have been designed which have been characterized as being bearing and seal-free. Such systems typically employ magnetic levitation means which is in effect an actual form of bearing, much the same as sleeve bearings, ball bearings, or other friction-inducing bearings. Such arrangements using magnetic bearings, while being operational and functional, may be rendered complex and accordingly require significant number of additional components including magnetic devices, position sensors, and rapid-response magnetic drive means. A number of such patents have been granted in the past, including those to Olsen et al. U.S. Pat. Nos. 4,688,998 and 5,195,877. The apparatus of the present invention, by contrast, is fully bearing and seal-free, with dynamic balance being achieved through a combination of hydrodynamic and buoyant forces.

Among the disadvantages inherent in pumps utilizing friction-reducing bearings include local heat generation such as may occur from the use of ball bearings, friction bearings, sleeve bearings, and the like. Low flow and high pressure may result in local areas due to the use of such structures. In addition, with all such bearing-equipped pumps, a high spring constant is provided wherein a small displacement of the rotor (or impeller) introduces very high forces which can damage or effectively destroy bearings. In addition, different forces are introduced in the structure whenever variations in axial positions occur.

In the present structure, the pump is bearing and seal-free, with the effective low compliance of the rotor allowing for relatively high displacement without the creation of large forces otherwise required to hold the rotor in its predetermined position. In addition, the rotor seeks and finds an equilibrium position which in certain situations can be off-set from the housing axis (in either the rotational or transverse axes) which typically occurs when the rotational axis of the pump is altered. Rotational movement of the pump housing will be manifested in displacement of the rotational or vertical axis of the rotor. The present arrangement has been found to eliminate the need for a highly precise axis in design, fabrication and operation. The lack of a positionally fixed rotational axis reduces the introduction of large forces which otherwise would be created when the axis of the rotor is shifted away from its normal centrally disposed position. In addition to the outer surface of the rotor core, one or more shrouds are arranged concentrically with the outer surface of the rotor core, with the configuration providing one or more annular channels for flow. In addition to this, introduction of the vanes acting as paddles between the core and the shroud or in the case of multiple shrouds, then between the shrouds, with this arrangement providing even more channels for flow through the rotor.

In the arrangement of the present invention, the pump includes a pumping chamber with a central axis, and with a rotor body being disposed within the chamber for bearing and seal-free rotation therewithin. The rotor has a double or dual-conical configuration which converges toward opposed polar regions, and with the axis of rotation extending between these polar regions. In addition to the rotor core, one or more concentric shrouds are provided to increase the area of contact between the fluid being pumped and the surface of the rotor, and to provide annular channels through which fluid flow may occur. Fluid inlet ports are arranged in the pumping chamber in oppositely disposed relationship within the chamber, with the fluid being transported or transferred to the inlet port area either externally or internally of the chamber. Except for those occasions when the rotor is displaced, it is normally arranged in coaxial relationship with both the pumping chamber and the fluid inlet ports. The outlet port or ports are arranged generally medially of the chamber, midway between the inlet ports and typically are positioned tangentially of the medial portion of the pumping chamber. In those situations where the axis of rotation of the rotor is arranged vertically, the dual-conical configuration is such that flow on the outside surface of the rotor core and in the annular channels proceeds downwardly on the upper portion, and upwardly on the lower portion of the dual-cone.

An example of an external transfer of fluids between the oppositely disposed fluid inlet ports is a fluid transfer line which introduces the fluids at opposite ends of the housing. As an example of an internal transfer, an internal bore may be provided which extends along the rotational axis of the rotor between opposite ends thereof, so as to permit transfer of fluids internally.

The term "oppositely disposed inlet ports" is intended to reflect the utilization of fluid introduction at opposite ends of the rotor, and is intended to include those arrangements wherein all of the fluid being pumped is initially introduced into one polar region of the housing, the fluid nevertheless is transferred either internally or externally to the oppositely disposed polar region.

The pump shown in the drawings is in operational mode with the rotor spinning about its axis of rotation and with all forces acting on the rotor balanced. In the stationary/non-operational mode with the fluid in the housing, only the buoyant forces are acting on the rotor, and the rotor floats up in the random position. In the stationary/non-operational mode with no fluid in the housing, the rotor is resting on the interior of the housing under gravitational forces.

Levitation of the rotor, as indicated, is achieved by a combination of hydrodynamic and buoyant forces. Briefly, the buoyant component is achieved as a result of careful selection of the rotor density, with the preferred relative density being between about 0.1 and 0.9 of the relative density of the fluid being pumped. The term "relative density" as will be appreciated, defines the density of the rotor which is measured relative to the density of the fluid being pumped. In a dynamic and operational mode, the buoyant forces merely become a component of lesser or secondary importance to the more significant and more highly effective hydrodynamic force.

The hydrodynamic force component is achieved as a result of the motion of the fluid as it is being moved through the pumping chamber. As the velocity of the fluid increases, the hydrodynamic forces increase substantially, and with the proper selection of rotor density, the hydrodynamic forces which are created during normal operation result in achieving a precise, steady and controllably repeatable centering of the rotor within the pumping chamber.

The intent of the present invention is to bring the fluid from the opposite inlet regions of the housing to the medial plane of the housing, combine two opposite flows in the medial plane, and deliver the fluid to the outlet port with a minimal damage and losses by avoiding turbulence, flow separation, sharp turns, stagnation, and other undesired conditions. This is achieved by having the main flows through the rotor channels, secondary flows between the inner periphery of the housing, and the outer periphery of the rotor shroud, bringing into coincidence the medial planes of the housing and the rotor, and by moving away the electromagnetic drive means plane from the median planes of the housing and the rotor to provide for improved coupling and flow.

The pump structure of the present invention has particular application for transferring fragile and/or aggressive liquids, in particular, for transferring human blood. Since certain components in blood are extremely fragile and are damaged upon exposure to external forces, conventional pumps are simply unsuited for the application. Additionally, conventional seals and/or bearings typically found within conventional pump structures pose substantial and significant threats to cell damage. A further feature of the pump of the present invention rendering the pump well suited for transfer of blood is its essentially friction-free operation. Any frictional force due to relative motion between the rotor and the stator creates the risk of generation of thermal energy, and thus may contribute to heat build-up. Since blood is extremely sensitive to temperature change, particularly any increase in temperature above conventional body temperature, reduction and/or virtual elimination of friction provides significant and substantial advantages.

Since the structure of the present invention does not require bearings, energy consumption is reduced through the elimination of energy losses otherwise occurring in the bearings, including energy lost in contact bearings as well as electrical losses in magnetic bearings. The driving forces for the impeller may be located generally in the plane of the center of gravity or center of mass of the impeller, or adjacent thereto and normal to the axis of rotation. This feature results in the creation of a gyroscopic effect of a free-body gyroscope, and the configuration of the present invention is such as to stabilize the impeller when the axis of the housing is rotated relative to the spin axis of the rotor. In other words, the spin axis of the rotor may be altered because of a change-of-position of the housing, and thus the spin axis may not always be about the vertical axis, but can be about the horizontal axis as well.

In addition to blood pump applications, the device of the present invention finds utility in connection with other fluids as well. Certainly non-delicate fluids may be appropriately treated and/or moved with pump devices of the present invention including the aggressive fluids as discussed hereinabove. Eliminating shafts, bearings and seals substantially reduces the manufacturing cost of the present pump. Also, the present pump has a virtual unlimited mechanical life under normal conditions. The device of the present invention finds utility for any fluids when economy, longevity, and uninterrupted service are the factors.

SUMMARY OF THE INVENTION

Therefore, it is a primary object of the present invention to provide an improved pump for transferring fragile liquids such as human blood, and wherein the pump is bearing and seal-free, with the rotor having at least one shroud in spaced relationship to the outer surface of the rotor core to create one or more annular flow channels, and with the rotor being dynamically balanced upon rotation by a combination of hydrodynamic and buoyant forces.

It is yet a further object of the present invention to provide an improved pump for application with human blood which is capable of creating a uniform and consistent flow of such liquids without damaging or otherwise adversely affecting the quality of the material being pumped.

It is yet a further object of the present invention to provide a pump structure utilizing a pumping chamber housing a shrouded rotor wherein rotation of the rotor is achieved by an electromagnetic drive system operating in conjunction with an array of permanent magnets disposed on the rotor in a brushless configuration.

Other and further objects of the present invention will become apparent to those skilled in the art upon a study of the following specification, appended claims, and accompanying drawings.

IN THE DRAWINGS

FIG. 1 is a perspective view of a pump assembly prepared in accordance with the present invention;

FIG. 2 is a vertical sectional view taken through the axis of the structure as illustrated in FIG. 1, and illustrating the configuration of the rotor including the rotor core and shroud, and with this view further illustrating the flow pattern created by the pump when in actual operation;

Figure 3:
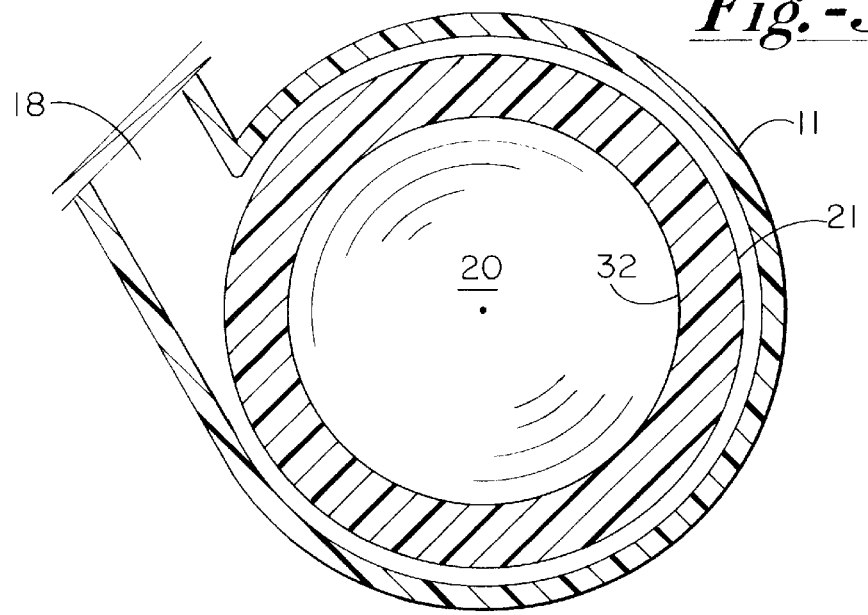
Figure 4:
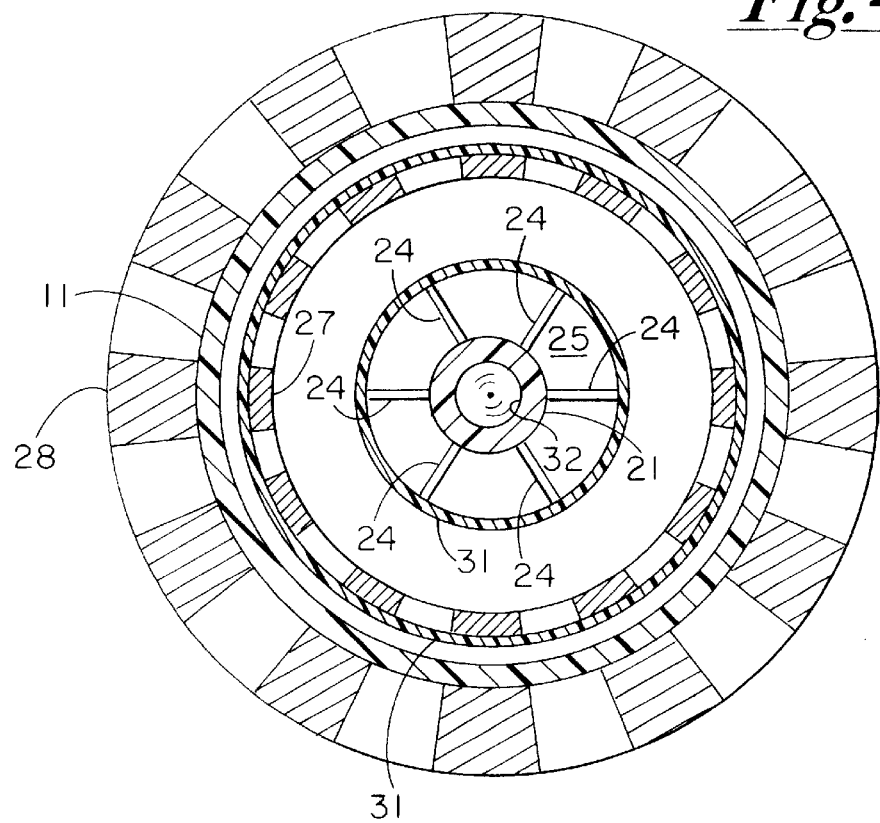
Figure 7:
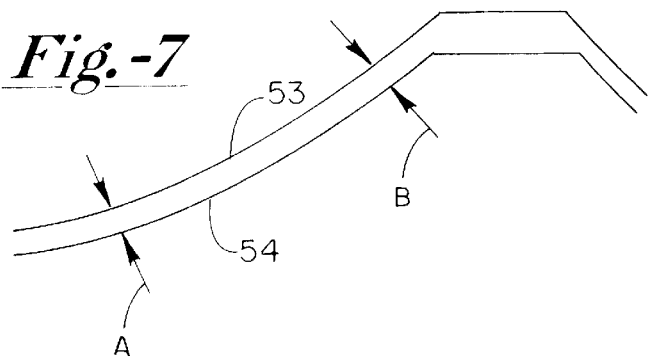
Figure 8:
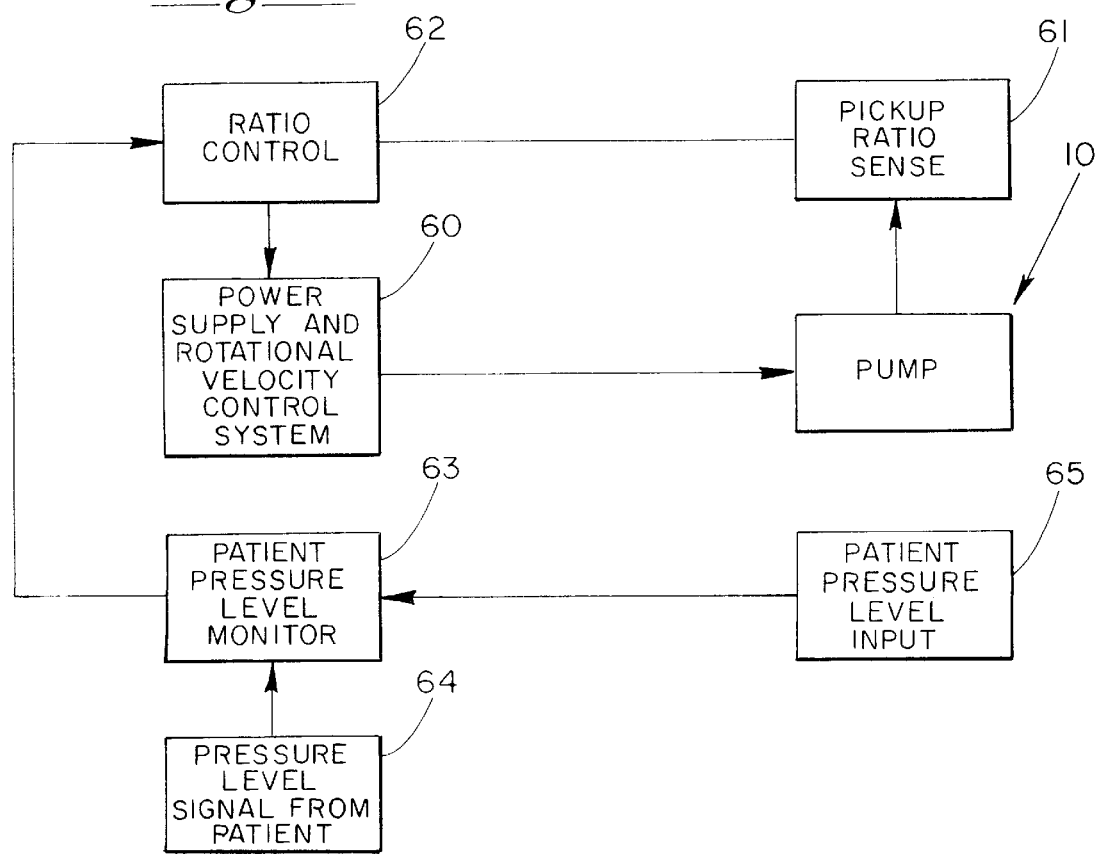

FIGS. 3 and 4 are horizontal sectional views taken along the line and in the direction of the arrows 3—3 and 4—4, respectively, of FIG. 2;

FIG. 5 is a view similar to FIG. 2, and illustrating a modified configuration for the drive components;

FIG. 6 is a view similar to FIG. 2 and illustrating a modified shroud configuration for the rotor;

FIG. 7 is a fragmentary sectional view taken on a slightly enlarged scale and illustrating the configuration of the clearance between the rotor and housing; and FIG. 8 is a schematic diagram illustrating a typical system in which the device of the present invention may function.

DESCRIPTION OF THE PREFERRED EMBODIMENT

In accordance with the preferred embodiment of the present invention, and with particular attention being directed to FIGS. 1, 2 and 3 of the drawings, the pump generally designated 10 comprises a housing 11, the interior of which defines pumping chamber shown generally at 12. In other words, the inner periphery 13 of housing 11 is the outer periphery of the chamber 12. As is clear from the views of FIGS. 2 and 3, housing 11 and chamber 12 share a central axis which extends along axis 14 as set forth in FIG. 2. Housing 11, and accordingly chamber 12, is provided with a pair of inlet ports as at 16 and 17, along with an outlet port as at 18. Inlet ports 16 and 17, collectively, define the inlets to the chamber, while outlet port 18 defines the outlet. The inlet ports 16 and 17 are arranged coaxially with the chamber, that is, along axis 14, with the inlet ports being arranged transverse to axis 14 and in oppositely disposed relationship to chamber 12. Outlet port 18 is arranged medially of the inlet ports, and is, as indicated, disposed generally transversely of axis 14.

With continued attention being directed to FIGS. 2 and 3 of the drawings, rotor generally shown at 20 is disposed within chamber 12 and has a symmetrical dual conical configuration. This configuration provides a core member 19 with dual cones converging toward opposed polar regions such as 19A and 19B, and the rotor is provided with an axis of rotation which extends between the polar regions. The base of each of the two cones forming the dual cone configuration of core 19 are coupled together and form a common center plane. Positioned between core 19 and shroud 23 are a plurality of vanes, with the opposed ends of the vanes being shown in FIG. 2. These vanes are also shown in section in FIG. 4. Coupled to core 19 is a shroud 23, with shroud 23 being coupled to core 19 by means of coupling rods or posts 24—24, thereby creating an additional fluid contact area for inducing flow, along with an annular flow channel as shown generally at 25. An external flow channel is also defined annularly and externally of rotor assembly 20 as at 26.

A plurality of permanent magnets are provided as at 27—27, with these magnets being arranged at radially spaced locations below or above the medial plane of rotor 20 and along the axis of rotation of the rotor, with the permanent magnets being provided at equally radially and arcuately spaced locations. Electromagnetic drive means are provided as at 28—28 and 29—29, with the electromagnetic drive means being, in turn, coupled to a source of electrical energy and arranged to deliver rotational driving energy to the rotor through the permanent magnets 27—27. The drive arrangement is, of course, commonly referred to as a brushless motor configuration and brushless motor drives are, of course, well known in the art. The rate of rotation of rotor 20 is conveniently controlled by means of the frequency of the field applied to electromagnetic members 28—28 and 29—29, with the rate of rotation being controlled by the frequency of the applied electromagnetic field, or by selective energization of the electromagnetic means 28—28 and 29—29. Such drives are, of course, commonly utilized and well known in the art.

Rotor 20 is further defined by walls 21 and 22 along with shroud 23, with the material of construction being either similar or identical to that employed in housing 11. A suitable biocompatible material such as polycarbonate, acrylic, or copolymers of polystyrene may be employed, or alternatively a coating may be applied to a suitable substrate in order to enhance the biocompatibility of the structure. In those instances where the device is not being employed for implantation, then, of course, other materials may be employed, provided that the blood-contacting surfaces be formed and/or coated with a non-thrombogenic material.

Rotor 20 is provided with a hollow core or void area internally of surface 32, with this area providing a means for controlling the relative density of the rotor body. Preferably, the relative density is selected by the ratio of the relative density of the rotor to that of the fluid being pumped, and in most applications, the relative density of the rotor to the fluid being pumped is between about 0.3 and 0.6, with it being understood that relative densities of between about 0.1 and 0.9 may be found useful. In the event the rotor material has a density which is lower than that of a fluid to be pumped, the voids in the core and shroud may, of course, be eliminated.

The dual conical configuration of rotor 20 and its shroud 23 provides the finished structure with an axial length along the axis of rotation as being generally equal to the axial length of the pumping chamber between the inlet ports 16 and 17. The transverse diameter of the rotor 20 is defined along a medial plane, as along medial line 33 and with the configuration of the dual converging cones providing a clearance between the surface of the shroud and the inner surface of the pumping chamber as illustrated in greater detail in FIG. 7. Generally speaking, the clearance as indicated at A—A and B—B is such that the clearance is shown substantially constant from the inlet port area to the outlet port area, however this clearance may also slightly diverge or converge toward the outlet. The dimensional clearance is sufficient to provide for a flow rate which is adequate to assure laminar flow between the zone of the polar tip to the medial plane. The design of the shroud is undertaken to assist in preserving such laminar flow. With these considerations in mind, the clearance between the inner surface of the pumping chamber and the periphery of the rotor shroud preferably ranges from between about 1 millimeter up to about 7 millimeters, with a narrower range of between about 1 millimeter and 3 millimeters being generally preferred. Generally, a clearance of about 1.5 millimeters between the outer surface of the shroud 23 and the inner surface 13 of housing 11 is preferred.

With respect to the areas of the inlet and outlet ports, it is generally preferred that the combined area of the inlet ports be at least generally equal to the area of the outlet port, thereby providing more consistency in flow and pressures, and also providing for an appropriate hydrodynamic balancing of the rotor 20 within the chamber 12. In the event multiple outlet ports are employed, then and in that event, it remains preferable that the combined area of the outlet ports be generally equal to the combined area of the inlet ports.

As has been indicated, the drive means for the electromagnetic drive elements 28—28 and 29—29 is preferably in the form of conductor windings, and for purposes of achieving appropriate hydrodynamic balance, the windings are carefully controlled and selectively made so as to preserve the hydrodynamic balance of the rotating rotor while eliminating the need for any form of bearing.

As has been indicated, the moment of inertia of the impeller is effectively minimized by virtue of the positioning of the mass of the impeller closer to the center of gravity (or center of mass). This may be obtained by moving the mass of the impeller needed for structural integrity closer to the center, and generally as closely as possible to the rotational axis. The moment of inertia may be controllably adjusted in connection with the structure of the present invention by arranging and mounting the permanent magnets within a circular or annular zone which is as close as possible to the maximum radius of the rotor shroud, as required, while increasing the strength of the structure along its axis of rotation. This feature is illustrated in FIG. 2 wherein the permanent magnets 27—27 are disposed adjacent the outer circumference of lower shroud segment 30.

Accordingly, in the configuration illustrated in FIG. 2, lower shroud segment 30, while concentrically arranged relative to rotor core 24, this segment of the shroud encloses or otherwise encapsulates permanent magnets 27—27, while at the same time arranging an annular flow channel as at 31.

With respect to the fluid being pumped, it should be noted that the human blood has a viscosity of about 4 centipoises at 25° C., and this viscosity is sufficient to provide for sufficient friction between a relatively smooth rotating surface and blood so as to achieve a sufficient rotational component of motion for hydrodynamic balancing. In the shrouded rotor configuration illustrated herein, it will be appreciated that the shroud provides additional contact area, thus accommodating the utilization of relatively smooth rotating surfaces and fluid blood.

As the rotational velocity of the fluid being pumped increases, its hydrodynamic balance effect will, of course, increase correspondingly and proportionately. With a rotational velocity of approximately 1000 rpm, the hydrodynamic balancing effect substantially overwhelms the buoyant effect afforded by the relative density of the rotor within the chamber.

For start-up purposes, saline is normally preferred as the functional material, with the saline being employed for a period of time until the desired rotational velocity is achieved, and thereafter blood may be introduced as the working solution being pumped and/or transferred.

While the rotor structure illustrated is described as being relatively smooth, vanes may be employed on the structure with the vanes forming arcuately spaced passages within the rotor. In other words, the vanes may be formed as individual arcuately spaced paddles to form spaced-apart fluid passages and/or channels. A plurality of vanes are positioned between the outer surface of core 19 and the inner surface of shroud 23 as illustrated in FIGS. 2 and 4. Additionally, if desired, the configuration of support may be such that these components of the assembly function as vanes as well. Thus, while vanes as illustrated have rounded edges, other vane configurations such as elliptical may be employed.

The inlet and outlet diameters are preferably 7 millimeters and the relative density is preferably between 0.1 to 0.9, with a relative density of 0.5 being preferred.

For most operational purposes, an inlet pressure ranging from between about 5 millimeters of Hg (mercury) up to about 40 millimeters Hg (mercury) is considered normal and appropriate for fluid dynamics dealing with human blood. Outlet pressures of between about 40 millimeters Hg (mercury) up to about 150 or 200 millimeters Hg (mercury) may be employed. When the device of the present invention is functioning as an implantable unit, the outlet pressure will, of course, depend upon the patient's activity and circulatory requirements being indicated.

Attention is now directed to FIG. 5 of the drawings wherein a modified drive and shroud configuration is illustrated. In FIG. 5, for example, shroud 40 is symmetrically arranged about rotor core 19. In this connection, however, both upper and lower portions of shroud 40 are symmetrical, and provide secondary annular flow channels as at 41 and 42. Additionally, main or primary annular flow channels are provided as at 43 and 44, as shown in the drawings.

In this arrangement, however, symmetrically arranged dual drive mechanisms are provided with permanent magnet assemblies being shown at 27A and 27B respectively, and with drive magnets being shown at 28A, 28B, 29A, and 29B, respectively. With the exception of the shroud design, the other features of the configuration of FIG. 5 are the same as those illustrated and described in connection with FIGS. 1 and 2 hereinabove.

With attention now being directed to FIG. 6 of the drawings, a modified shroud configuration is illustrated, with rotor core 19 being provided with a pair of concentrically arranged shrouds as at 45 and 46 respectively. In the arrangement of FIG. 6, it will be noted that inner shroud 45 is totally symmetrical about rotor core 19, while outer shroud 46 is provided with a lower segment or portion as at 47 which is similar in its configuration to shroud portion 30 as illustrated in FIG. 2. In the configuration of FIG. 6, multiple annular flow channels are provided between the rotor core and the inner shroud as at 48, between inner and outer shrouds as at 49, and in the outer annular zone between outer shroud 46 and the inner surface 50 of housing 11, with this outer annular channel being shown at 51. The rotor configuration with multiple shrouds as shown in FIG. 6 may be modified in the manner of the structure illustrated in FIG. 5 with a dual drive mechanism.

With attention now being directed to FIG. 7 of the drawings, this figure, which is a fragmentary sectional view, illustrates the configuration of the clearance between the outer surface of the rotor shroud and the housing. In this view, the inner surface of the housing is illustrated at 53, with the outer surface of the shroud being illustrated at 54.

Attention is now redirected to FIG. 6 of the drawings wherein the pump 10 is coupled in a system which functions as a ventricular or heart-assist device. Pump 10 is powered by power supply 60 and sensors, including pickup ratio sensor 61 and ratio control 62 are employed. The patient pressure level monitor 63 provides an input to ratio control 62 with the level monitor receiving information including patient pressure level input as at 64 and pressure level signal 65. These systems are known in the art and may be employed effectively in connection with the device of the present invention.

While double shrouds have been discussed, it is possible that multiple shrouds may be employed wherein the rotor core is provided with surfaces of revolution disposed axially outwardly of the outer core surface, and with the surfaces of revolution being arranged coaxially with the axis of rotation of the rotor.

While the term "double conical configuration" has been employed throughout for the rotor core, it will be understood that other surfaces of revolution may be employed, such as those surfaces of revolution generated by a curved line such as parabola, or a straight line so as to form a cone. Thus, the term "cone" is understood to be broadly defined herein. Additionally, modified surfaces of revolution such as those illustrated in connection with the shroud of FIG. 5 may be utilized.

It will be appreciated, of course, that various modifications may be made in the preferred embodiment illustrated above, and these modifications may be made without actually departing from the spirit and scope of the present invention.

What is claimed is:

1. A pump for transferring fluids and comprising a pumping chamber with an inner periphery, an outer periphery and a central axis, a pair of fluid inlet ports arranged in oppositely disposed relationship on said chamber and coaxially with said pumping chamber, an outlet port means arranged transversely and generally medially of said pair of inlet ports, a rotor assembly disposed within said pumping chamber and having a core portion with a dual conical configuration converging toward opposed polar regions and with the rotor assembly having an axis of rotation extending between said polar regions and arranged coaxially with the axis of said pumping chamber, magnetic driven means arranged on said rotor assembly at radially spaced locations generally about said axis of rotation, electromagnetic drive means coupled to a source of energy and arranged to deliver rotational driving energy to said rotor assembly through said magnetic driven means; said rotor assembly comprising:

(a) a rotor core portion defining a first surface of revolution having an outer peripheral surface and a central axis extending therethrough;

(b) at least one shroud coupled to the outer surface of said rotor core portion with said shroud defining a second surface of revolution arranged coaxially with the central axis of said rotor core portion, said shroud having an inner surface spaced from the outer surface of said rotor core portion and defining flow channels disposed annularly inwardly and annularly outwardly of said second surface of revolution;

(c) said rotor assembly having a density relative to the fluid being pumped therein of between about 0.1 and 0.9;

(d) said second surface of revolution having a configuration with an axial length extending along said axis of revolution and defining the axial length of said pumping chamber disposed between said inlet ports; and (e) with the diameter of said rotor assembly transverse to said axis of rotation defining a medial plane and being selected to provide a clearance between the outer surface of said rotor core and the inner surface of said pumping chamber, and with the magnitude of the clearance between said inner surface of said pumping chamber and the outer periphery of said rotor core portion ranging from slightly divergent to slightly convergent.

2. The pump of claim 1 wherein said rotor assembly includes at least two shroud members, with each shroud member being mounted for rotation with said rotor core and defining three annularly spaced-apart flow channels equal in number to the number of shrouds plus one.

3. The pump of claim 1 wherein the rate of rotation of said rotor is controllably variable.

4. The pump of claim 1 being particularly characterized in that means are provided for sensing the rotational velocity of said rotor assembly.

5. The pump of claim 1 being particularly characterized in that the driving forces for said rotor assembly are coupled to magnetic driven means disposed in spaced relationship to the center of mass of the rotor assembly.

6. The pump of claim 1 being particularly characterized in that the fluid flows from inlets adjacent the polar tips of the cones to said outlet adjacent the medial plane.

7. The pump as defined in claim 1 wherein the drive means includes permanent magnets arranged within the rotor along radial points adjacent the outer circumference of the rotor assembly.

8. The pump as defined in claim 1 wherein the drive means includes permanent magnets disposed in a circular array, and wherein the outer perimeter of the magnets forming the array is disposed radially inwardly from the outer circumference of the rotor assembly and in a plane spaced from the plane of said outlet, and with the structural mass of the rotor being disposed adjacent the rotational axis, thereby reducing the moment of inertia of said rotor assembly.

9. A pump for transferring fluids and comprising a pumping chamber with an inner periphery, an outer periphery and a central axis, inlet port means arranged in polar relationship to said pumping chamber and coaxially with said pumping chamber, an outlet port means arranged transversely and generally medially of said pair of inlet ports, a rotor assembly disposed within said pumping chamber and having a core portion with a dual conical configuration converging toward opposed polar regions and having an axis of rotation extending between said polar regions and arranged coaxially with the axis of said pumping chamber, magnetic driven means arranged on said rotor at radially spaced locations from said axis of rotation, electromagnetic drive means coupled to a source of energy and arranged to deliver rotational driving energy to said rotor assembly through said magnetic driven means; said rotor assembly comprising:

(a) a rotor core portion defining a first surface of revolution having an outer peripheral surface and a central axis extending therethrough;

(b) at least one shroud coupled to the outer surface of said rotor core portion with said shroud defining a second surface of revolution arranged coaxially with the central axis of said rotor core portion, said shroud having an inner surface spaced from the outer surface of said rotor core portion and defining flow channels disposed annularly inwardly and annularly outwardly of said second surface of revolution;

(c) said rotor assembly having a density relative to the fluid being pumped therein of between about 0.1 and 0.9;

(d) said second surface of revolution having a configuration with an axial length extending along said axis of revolution and defining the axial length of said pumping chamber disposed between said inlet ports;

(e) with the diameter of said rotor assembly transverse to said axis of rotation defining a medial plane and being selected to provide a clearance between the outer surface of said rotor core and the inner surface of said pumping chamber, and with the magnitude of the clearance between said inner surface of said pumping chamber and the outer periphery of said rotor core portion ranging from slightly divergent to slightly convergent; and (f) the arrangement being such that the sole support for the rotor are the hydrodynamic forces created in the fluid being pumped, wherein the casing structure of the pump is free of rotor supporting members and bearings.

* * * * *